(12) United States Patent
Trolinder et al.

(10) Patent No.: US 6,818,807 B2
(45) Date of Patent: Nov. 16, 2004

(54) HERBICIDE TOLERANT COTTON PLANTS HAVING EVENT EE-GH1

(75) Inventors: Linda Trolinder, Idalout, TX (US); Jefferson Gwyn, Greenville, MS (US); Marc Debeuckeleer, Zwijnaarde (BE)

(73) Assignee: Bayer BioScience N.V. (BE)

( * ) Notice: Subject to any disclaimer, the term of this patent is extended or adjusted under 35 U.S.C. 154(b) by 0 days.

(21) Appl. No.: 09/921,922

(22) Filed: Aug. 6, 2001

(65) Prior Publication Data

US 2003/0097687 A1 May 22, 2003

(51) Int. Cl.$^7$ .............................. A01H 5/00; A01H 5/10; C12N 15/82
(52) U.S. Cl. ........................ 800/300; 800/298; 800/314
(58) Field of Search .................................. 435/468, 419, 435/418; 800/278, 300, 314, 298

(56) References Cited

U.S. PATENT DOCUMENTS

| | | | |
|---|---|---|---|
| 5,159,135 A | 10/1992 | Umbeck | 800/314 |
| 5,986,181 A | 11/1999 | Trolinder et al. | 800/314 |

FOREIGN PATENT DOCUMENTS

| | | |
|---|---|---|
| WO | WO 92/09696 | 6/1992 |
| WO | WO 98/15622 | 4/1998 |
| WO | WO 00/26345 | 5/2000 |
| WO | WO 00/26356 | 5/2000 |
| WO | WO 00/71733 | 11/2000 |
| WO | WO 01/31042 | 5/2001 |
| WO | WO 01/51654 | 7/2001 |

OTHER PUBLICATIONS

Puchta et al 1996, Trends in Plant Science 1(10):340–348.*
G. Keller et al., Transgenic Research 6, pp. 385–392 (1997), "Transgenic cotton resistant to herbicide bialaphos".
M. De Block et al., The EMBO Journal, vol. 6, No. 9, pp. 2513–2518, 1987, "Engineering herbicide resistance in plants by expression of a detoxifying enzyme".
Lesli K. Blair–Kerth, "Tolerance of transformed cotton to glufosinate," Weed Science, 49: pp. 375–380, 2001.
Yao–Guang Liu, "Efficient isolation and mapping of *Arabidopsis thaiana* T–DNA insert junctions by thermal asymmetric interlaced PCR," The Plant Journal (1995) 8(3), pp. 457–463.

* cited by examiner

*Primary Examiner*—David H Kruse
(74) *Attorney, Agent, or Firm*—Hunton & Williams LLP

(57) ABSTRACT

The invention pertains to transgenic cotton plants, plant material and seeds, characterized by having the EE-GH1 transformation event, particularly by the presence of a gene encoding a protein that confers herbicide tolerance, at a specific location in the cotton genome. The cotton plants of the invention combine the herbicide tolerant phenotype with optimal agronomic performance.

10 Claims, 1 Drawing Sheet

HERBICIDE TOLERANT COTTON PLANTS HAVING EVENT EE-GH1

FIELD OF THE INVENTION

This invention pertains to transgenic cotton plants, plant material and seeds, characterized by harboring a specific transformation event, particularly by the presence of a gene encoding a protein that confers herbicide tolerance, at a specific location in the cotton genome. The cotton plants of the invention combine the herbicide tolerant phenotype with an agronomic performance, genetic stability and adaptability to different genetic backgrounds equivalent to the non-transformed cotton line in the absence of weed pressure.

All documents cited herein are hereby incorporated herein by reference.

BACKGROUND OF THE INVENTION

The phenotypic expression of a transgene in a plant is determined both by the structure of the gene itself and by its location in the plant genome. At the same time the presence of the transgene at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials.

Cotton fiber is the single most important textile worldwide. About 80 million acres of cotton are harvested annually across the globe. Cotton is the fifth largest crop in the U.S. in terms of acreage production, with over 15 million acres planted in 2000. Primary weed species for cotton are *Ipomoea* sp. (morning glory), *Amaranthus* spp. (pigweed), *Cyperus* spp. (nutsedge), *Xanthium* spp. (cocklebur) and *Sorghum* spp. (johnsongrass). Before the introduction of broad-leaf herbicides that could be used on a growing cotton field, growers used directed, post-emergence applications of nonselective herbicides taking care not to contact the growing crop plants. As this requires a difference in height between the weeds and the crop, this is not always possible. Especially for small cotton, this practice is time-consuming and potentially damaging to the crop.

The bar gene (Thompson et al, 1987, EMBO J 6:2519–2523; Deblock et al. 1987, EMBO J. 6:2513–2518) is a gene encoding the enzyme phosphinothricin acetyl transferase (PAT), which, when expressed in a plant, confers resistance to the herbicidal compounds phosphinothricin (also called glufosinate) or bialaphos (see also for example U.S. Pat. Nos. 5,646,024 and 5,561,236) and salts and optical isomers thereof. Phosphinothricin controls broadleaf weeds including morning glory and has a wide window of application.

Successful genetic transformation of cotton has been obtained by a number of methods including Agrobacterium infection of cotton explants (Firoozabady et al. 1987, Plant Molecular Biology 10:105–116; Umbeck et al. 1987, Bio/Technology 5:263–266 and in WO 00/71733, U.S. Pat. No. 5,004,863, and U.S. Pat. No. 5,159,135), as well as direct gene transfer by microprojectile bombardment of meristematic cotton tissues (Finer and Mc Mullen, 1990, Plant Cell Reports, 5:586–589; McCabe and Martinell, 1993, Bio/Technology 11:596–598, WO92/15675, EP0 531 506). Increased transformation efficiency for Agrobacterium transformation has been reported using the methods described by Hansen et al. (1994, Proc. Nat. Acad. Sci. 91:7603–7607) Veluthambi et al. (1989, Journal of Bacteriology 171:3696–3703) and WO 00/71733.

Different methods for regeneration of cotton plants have also been described (WO 89/05344, U.S. Pat. No. 5,244,802, U.S. Pat. No. 5,583,036, WO89/12102, WO98/15622, and WO97/12512).

However, the foregoing documents fail to teach or suggest the present invention.

SUMMARY OF THE INVENTION

The present invention relates to a transgenic cotton plant, or seed, cells or tissues thereof, comprising, stably integrated into its genome, an expression cassette which comprises a herbicide tolerance gene comprising the coding sequence of the bar gene (as described in Example 1.1 herein), which is herbicide tolerant and, in the absence of weed pressure, has an agronomic performance which is substantially equivalent to the non-transgenic isoline. Under weed pressure and the appropriate Liberty™ treatment, the plant will have a superior agronomic phenotype compared to the non-transgenic plant.

In one embodiment of the invention, the cotton plant or seed, cells or tissues thereof, comprises the expression cassette of pGSV71 (as described in Example 1.1, Table 1 herein). In the preferred embodiment of the invention the cotton plant or seed, cells or tissues thereof comprise elite event EE-GH1.

In another embodiment of the invention, the transgenic cotton plant or seed, cells or tissues thereof comprises:
  (i) event EE-GH1 in its genome ;or
  (ii) event EE-GH1 with the proviso that the bar gene used in the event is substituted with a nucleic acid sequence that hybridizes to the complement of the bar gene under stringent conditions.

More specifically, the present invention relates to a transgenic cotton plant, seed, cells or tissues thereof, the genomic DNA of which is characterized by the fact that, when analyzed in a PCR identification protocol as described herein, using two primers directed to the 5' or 3' flanking region of EE-GH1 and the foreign DNA, respectively, yields a fragment which is specific for EE-GH1. Preferably the primers are directed against the 5' flanking region within SEQ ID NO: 1 and the foreign DNA respectively; most preferably, the primers comprise the nucleotide sequence of SEQ ID NO: 2 and SEQ ID NO: 3 respectively, and yield a DNA fragment of between 250 and 290 bp, preferably of about 269 bp.

Reference seed comprising the elite event of the invention has been deposited at the ATCC under accession number PTA-3343. Thus, a preferred embodiment of the invention is the seed comprising elite event EE-GH1 deposited as ATTC accession number PTA-3343, which will grow into a cotton plant resistant to glufosinate. The seed of ATCC deposit number PTA-3343, which is a seed lot consisting of about 50% non-transgenic kernels and 50% transgenic kernels hemizygous for the transgene, comprising the elite event of the invention, which will grow into glufosinate tolerant plants. The seed can be sown and the growing plants can be treated with PPT or Liberty™ as described herein to obtain 100% glufosinate tolerant plants, comprising the elite event of the invention. The invention further relates to cells, tissues, progeny, and descendants from a plant comprising the elite event of the invention grown from the seed deposited at the ATCC having accession number PTA-3343. The invention further relates to plants obtainable by propagation of and/or breeding with a cotton plant comprising the elite event of the invention grown from the seed deposited at the ATCC having accession number PTA-3343.

The invention further relates to plants, seeds, cells or tissues comprising a foreign DNA sequence, preferably a herbicide tolerance gene as described herein, integrated into the chromosomal DNA in a region which comprises the plant DNA sequence of SEQ ID NO: 1 and/or SEQ ID NO: 4, more particularly which comprises the DNA sequence of SEQ ID NO: 5, or a sequence which hybridizes under stringent conditions to a sequence that is complementary to a sequence comprising the plant DNA sequence of SEQ ID NO: 1, SEQ ID NO: 4 and/or SEQ ID NO: 5.

The invention further provides a process for producing a transgenic cell of a cotton plant, which comprises inserting a recombinant DNA molecule into a region of the chromosomal DNA of a cotton cell, tissue or callus which comprises the plant DNA sequence of SEQ ID NO: 1 and/or SEQ ID NO: 4, more particularly which comprises the DNA sequence of SEQ ID NO: 5, or which comprises a sequence which hybridizes under stringent conditions to a sequence that is complementary to a sequence comprising the plant DNA sequence of SEQ ID NO: 1, SEQ ID NO: 4 and/or SEQ ID NO: 5.

The invention further relates to a method for identifying a transgenic plant, or cells or tissues thereof, comprising elite event EE-GH1 which method is based on identifying the presence of characterizing DNA sequences or amino acids encoded by such DNA sequences in the transgenic plant, cells or tissues.

According to one preferred aspect of the invention, the method for identifying a transgenic plant, or cells or tissues thereof, comprising elite event EE-GH1, comprises amplifying a sequence of a nucleic acid present in biological samples, using a polymerase chain reaction, with at least two primers, one of which recognizes the plant DNA in the 5' or 3' flanking region of EE-GH1, the other which recognizes a sequence within the foreign DNA. Preferably, the genomic DNA is analyzed using primers which recognize a sequence within the plant 5' flanking region of EE-GH1, most preferably within the plant DNA sequence in SEQ ID NO: 1, and a sequence within the foreign DNA, respectively. Especially preferably, the genomic DNA is analyzed according to the PCR identification protocol described herein whereby the primer recognizing a sequence within the 5' flanking region comprises the nucleotide sequence of SEQ ID NO: 2.

Particularly, the primer recognizing a sequence within the 5' flanking region comprises the nucleotide sequence of SEQ ID NO: 2 and the primer recognizing a sequence within the foreign DNA comprises the nucleotide sequence of SEQ ID NO: 3, so that the amplified fragment is a fragment preferably of between 250 and 290 bp, preferably of about 269 bp.

Accordingly, the present invention relates to the transgenic plant, cells or tissues thereof which can be identified according the above-described identification method for EE-GH1.

The present invention relates to methods for identifying elite event EE-GH1 in biological samples, which methods are based on primers or probes that specifically recognize the 5' and/or 3' flanking sequence of EE-GH1. In a preferred embodiment of the invention these methods are based on primers or probes which recognize a sequence within SEQ ID NO: 1 and/or SEQ ID NO: 4, more particularly primers or probes comprising the sequence of SEQ ID NO: 2.

The present invention further relates to the specific flanking sequences of EE-GH1 described herein, which can be used to develop specific identification methods for EE-GH1 in biological samples. More particularly, the invention relates to the 5' and or 3' flanking regions of EE-GH1, which can be used for the development of specific primers and probes as well as to the specific primers and probes developed from the 5' and/or 3' flanking sequences of EE-GH1. The invention further relates to identification methods for the presence of EE-GH1 in biological samples based on the use of such specific primers or probes.

The invention thus also relates to a kit for identifying elite event EE-GH1 in biological samples, the kit comprising at least one primer or probe which specifically recognizes the 5' or 3' flanking region of EE-GH1.

The invention also relates to a kit for identifying elite event EE-GH1 in biological samples, which kit comprises at least one specific primer or probe having a sequence which corresponds (or is complementary to) a sequence that hybridizes under stringent conditions to a specific region of EE-GH1. Preferably the sequence of the probe corresponds to a specific region comprising part of the 5' or 3' flanking region of EE-GH1. Most preferably the specific probe has (or is complementary to) a sequence that hybridizes under stringent conditions to the plant DNA sequence within SEQ ID NO: 1 or SEQ ID NO: 4.

Preferably the kit of the invention comprises, in addition to a primer which specifically recognizes the 5' or 3' flanking region of EE-GH1, a second primer which specifically recognizes a sequence within the foreign DNA of EE-GH1, for use in a PCR identification protocol. Preferably, the kit of the invention comprises two (or more) specific primers, one of which recognizes a sequence within the 5' flanking region of EE-GH1, most preferably a sequence within the plant DNA region of SEQ ID NO: 1, and an other which recognizes a sequence within the foreign DNA. Especially preferably, the primer recognizing the plant DNA sequence within 5' flanking region comprises the nucleotide sequence of SEQ ID NO: 2. Particularly, the primer recognizing the plant DNA sequence within 5' flanking region comprises the nucleotide sequence of SEQ ID NO: 2 and the primer recognizing the foreign DNA comprises the nucleotide sequence of SEQ ID NO: 1 described herein.

The methods and kits encompassed by the present invention can be used for different purposes such as, but not limited to the following: to identify EE-GH1 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising EE-GH1.

The present invention further relates to a method for tracking plants comprising elite event EE-GH1 in their genome upon introduction into different cultivars.

It will be understood that particular embodiments of the invention are described by the dependent claims cited herein.

BRIEF DESCRIPTION OF THE FIGURE

The following detailed description, given by way of example, but not intended to limit the invention to specific embodiments described, may be understood in conjunction with the accompanying Figure, incorporated herein by reference, in which.

DETAILED DESCRIPTION OF THE PREFERRED EMBODIMENT

Figure 1:
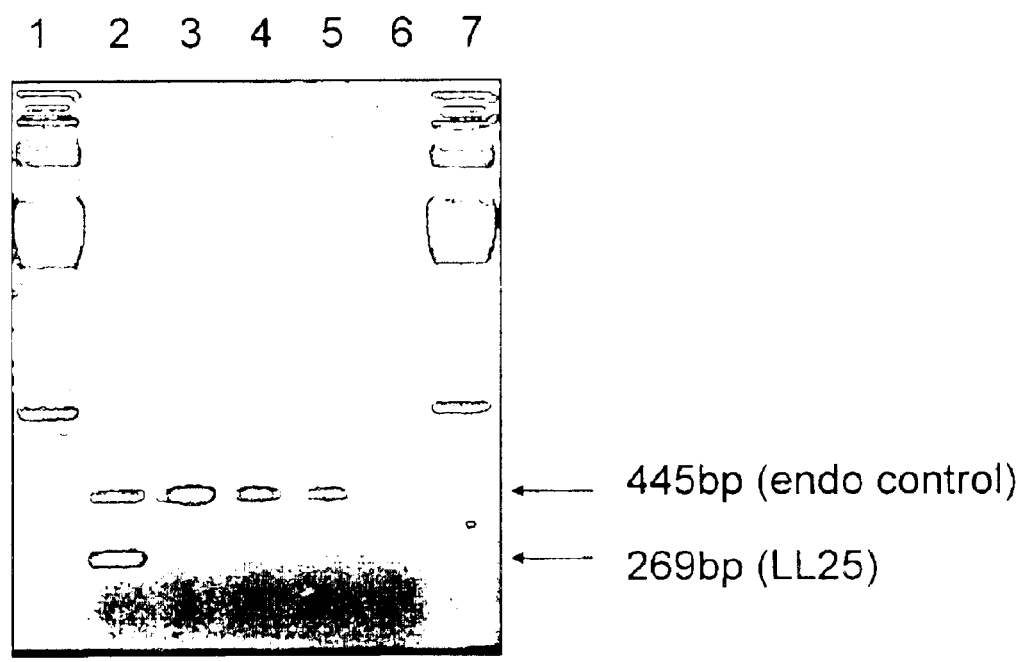
FIG. 1. PCR analysis of other events and elite event EE-GH1 using the EE-GH1 PCR identification protocol. Loading sequence of the gel: lane 1, molecular weight marker (100 bp ladder), lane 2, DNA sample from a cotton plant comprising the transgenic event EE-GH1, lane 3, DNA samples from a cotton plant comprising another transgenic event, lane 4, DNA from wild-type cotton, lane 5, wild-type+1 copy of the pGSV71-BamHI digest (positive control), lane 6, negative control (no template), lane 8, molecular weight marker (100 bp ladder).

The term "gene" as used herein refers to any DNA sequence comprising several operably linked DNA fragments such as a promoter region, a 5' untranslated region (the 5'UTR), a coding region (which may or may not code for a protein), and an untranslated 3' region (3'UTR) comprising a polyadenylation site. Typically in plant cells, the 5'UTR, the coding region and the 3'UTR are transcribed into an RNA of which, in the case of a protein encoding gene, the coding region is translated into a protein. A gene may include additional DNA fragments such as, for example, introns. As used herein, a genetic locus is the position of a given gene in the genome of a plant.

The term "chimeric" when referring to a gene or DNA sequence is used to refer to the fact that the gene or DNA sequence comprises at least two functionally relevant DNA fragments (such as promoter, 5'UTR, coding region, 3'UTR, intron) that are not naturally associated with each other and/or originate, for example, from different sources. "Foreign" referring to a gene or DNA sequence with respect to a plant species is used to indicate that the gene or DNA sequence is not naturally found in that plant species, or is not naturally found in that genetic locus in that plant species. The term "foreign DNA" will be used herein to refer to a DNA sequence as it has incorporated into the genome of a plant as a result of transformation. The "transforming DNA" as used herein refers to a recombinant DNA molecule used for transformation. The transforming DNA usually comprises at least one "gene of interest" (e.g. a chimeric gene) which is capable of conferring one or more specific characteristics to the transformed plant. The term "recombinant DNA molecule" is used to exemplify and thus can include an isolated nucleic acid molecule which can be DNA and which can be obtained through recombinant or other procedures.

As used herein the term "transgene" refers to a gene of interest as incorporated in the genome of a plant. A "transgenic plant" refers to a plant comprising at least one transgene in the genome of all of its cells.

The foreign DNA present in the plants of the present invention will preferably comprise a herbicide tolerance gene, more specifically a 35S-bar gene as the gene of interest.

A "herbicide tolerance" gene as used herein refers to a gene that renders the plant tolerant to a herbicide. An example of a herbicide tolerance gene is gene comprising a sequence encoding the enzyme phosphinothricin acetyl transferase, which detoxifies phosphinothricin, under the control of a constitutive promoter. More specifically, in the elite event of the present invention the herbicide tolerance gene comprises the coding sequence of the bialaphos resistance gene (bar) of *Streptomyces hygroscopicus* (Thompson et al. (1987) EMBO J 6: 2519–2523) under control of the 35S promoter from Cauliflower Mosaic Virus (Odell et al., (1985), Nature 313: 810–812), also referred to as "35S-bar" herein. The expression of the 35S-bar gene confers tolerance to herbicidal compounds phosphinothricin or bialaphos or glufosinate, or more generally, glutamine synthase inhibitors, or salts or optical isomers thereof which will generally be referred to as "glufosinate tolerance" herein.

By hybridizing under "stringent conditions" is meant the conventional hybridizing conditions as described by Sambrook et al. (1989) (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2× Denhardt's reagent and 0.1% SDS, or for 1 to 2 hours at 68° C. in 6×SSC, 2× Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2 ×SSC, 0.1% SDS, and 7) exposing the filter for 24 to 48 hours to X-ray film at −70° C. with an intensifying screen.

The incorporation of a recombinant DNA molecule in the plant genome typically results from transformation of a cell, tissue or callus (or from another genetic manipulation). The particular site of incorporation is either random or is at a predetermined location (if a process of targeted integration is used).

The DNA introduced into the plant genome as a result of transformation of a plant cell or tissue with a recombinant DNA or "transforming DNA" is hereinafter referred to as "foreign DNA" comprising one or more "transgenes". Thus, foreign DNA may comprise both recombinant DNA as well as newly introduced, rearranged DNA of the plant. However, the term "plant DNA" in the context of the present invention will refer to DNA of the plant which is generally found in the same genetic locus in the corresponding wild-type plant.

The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA present in a transgenic plant is introduced into a different plant through traditional crossing, its insertion site in the plant genome, or its flanking regions will generally not be changed (apart from occasional changes due to mutations or cross-over and transposons). An "insertion region" as used herein refers to the region corresponding to the region of at least 40 bp, preferably at least 100 bp, and up to more than 10000 bp, encompassed by the sequence which comprises the upstream and/or the downstream flanking region of a foreign DNA in the (untransformed) plant genome (and including the insertion site and possible target site deletion). Taking into consideration minor differences due to mutations within a species, an insertion region will retain at least 85%, preferably 90%, more preferably 95%, and most preferably 100% sequence identity with the sequence comprising the upstream and downstream flanking regions of the foreign DNA in a given plant of that species.

Expression of a gene of interest refers to the fact that the gene confers on the plant one or more phenotypic traits (e.g. herbicide tolerance) that were intended to be conferred by the introduction of the recombinant DNA molecule—the transforming DNA—used during transformation (on the basis of the structure and function of part or all of the gene(s) of interest).

An "event" is defined as a (artificial) genetic locus that, as a result of genetic engineering, carries a foreign DNA comprising at least one copy of the gene(s) of interest (also referred to as a transformation event). An event is characterized phenotypically by the expression of the transgenes. At the genetic level, an event is part of the genetic makeup of a plant. At the molecular level, an event is characterized by the restriction map (e.g. as determined by Southern blotting) and/or by the upstream and/or downstream flanking sequences of the foreign DNA, and/or the molecular configuration of the foreign DNA comprising the transgenes. Usually when transforming a plant cell, tissue or callus with a transforming DNA, a multitude of events are generated, each of which is unique.

An "elite event", as used herein, is an event which is selected from a group of events, obtained by transformation with the same transforming DNA or by back-crossing with plants obtained by such transformation, based on the phenotypic expression and stability of the transgenes and the absence of negative impact on the agronomic characteristics of the plant comprising it (i.e., selected transformation event). Thus the criteria for elite event selection are one or more, preferably two or more, advantageously all of the following:

a) That the presence of the foreign DNA in the plant does not compromise other desired characteristics of the plant, such as those relating to agronomic performance or commercial value;

b) That the event is characterized by a well defined molecular configuration which is stably inherited and for which appropriate diagnostic tools for identity control can be developed;

c) That the gene(s) of interest show(s) an appropriate and stable spatial and temporal phenotypic expression in homozygous condition of the event, at a commercially acceptable level in a range of environmental conditions in which the plants carrying the event are likely to be exposed in normal agronomic use.

It is preferred that the foreign DNA is associated with a position in the plant genome that allows introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which answers to the above-described criteria. A plant, plant material or progeny such as seeds can comprise one or more elite events in its genome. Thus, when referring to a plant, seed cell or tissue comprising elite event EE-GH1 in its genome, a plant, seed cell or tissue is intended which comprises the foreign DNA described herein (comprising the 35S-bar gene) integrated in its genome at the integration site described herein.

The tools developed to identify an elite event or the plant or plant material comprising an elite event, or products which comprise plant material comprising the elite event are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers" one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment") is amplified from a nucleic acid sample comprising the elite event. This means that only the targeted integration fragment, and no other sequence (of that size) in the plant genome or foreign DNA, is amplified under optimized PCR conditions.

Preferably, the integration fragment has a length of between 50 and 500 nucleotides, most preferably of between 100 and 350 nucleotides. Preferably the specific primers have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

As the sequence of the primers and their recognized sequence in the genome are unique for the elite event, amplification of the integration fragment will occur only in biological samples comprising (the nucleic acid of) the elite event. Preferably when performing a PCR to identify the presence of EE-GH1 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in 'PCR Applications Manual" (Roche Molecular Biochemicals, 2nd Edition, 1999). The optimal conditions for the PCR, including the sequence of the specific primers, is specified in a "PCR identification protocol" for each elite event. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying EE-GH1 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of EE-GH1. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event possibly also comprising part of the foreign DNA contiguous therewith (hereinafter also referred to as a "specific region" of the event). Preferably, the specific probe comprises a sequence of between 50 and 500 bp, preferably of 100 to 350 bp which hybridizes under stringent conditions to the nucleotide sequence (or the complement of such sequence) of a specific region. Preferably, the specific probe will comprise a sequence of about 15 to about 100 contiguous nucleotides identical (or complementary) to a specific region of the elite event.

A "restriction map" as used herein refers to a set of Southern blot patterns obtained after cleaving plant genomic DNA (and/or the foreign DNA comprised therein) with a particular restriction enzyme, or set of restriction enzymes and hybridization with a probe sharing sequence similarity with the foreign DNA under standard stringency conditions. Standard stringency conditions as used herein refers to the conditions for hybridization described herein or to the conventional hybridizing conditions as described by Sambrook et al. (1989) (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2× Denhardt's reagent and 0.1% SDS, or for 1 to 2 hours at 68° C. in 6×SSC, 2× Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

Due to the (endogenous) restriction sites present in a plant genome prior to incorporation of the foreign DNA, insertion of a foreign DNA will alter the specific restriction map of that genome. Thus, a particular transformant or progeny derived thereof can be identified by one or more specific restriction patterns.

Alternatively, plants or plant material comprising an elite event can be identified by testing according to a PCR identification protocol. This is a PCR which specifically recognizes the elite event. Essentially, a set of PCR primers is developed which recognizes a) a sequence within the 3' or 5' flanking sequence of the elite event and b) a sequence within the foreign DNA, which primers amplify a fragment (integration fragment) preferably of between 100 and 300 nucleotides. Preferably, a control is included of a set of primers which amplifies a fragment within a housekeeping gene of the plant species (preferably a fragment which is larger than the amplified integration fragment). The optimal conditions for the PCR, including the sequence of the specific primers is specified in a PCR identification protocol.

Other methods for identifying plants, plant material or products comprising plant material comprising elite event EE-GH1 are also envisaged. These methods include all methods based on the detection of the foreign DNA sequence and flanking sequence(s) of the elite event with a specific probe. More particularly, chip-based technologies, such as those described by Hacia et al. 1996 (Nat Genet 14(4):441–447) and Shoemaker et al. 1996 (Nat Genet 14(4):450–456) are envisaged. These methods allow segregation of target molecules as high-density arrays by using fixed probe arrays or by tagging of the genes with oligonucleotides, after which they can be screened by hybridization.

Identification of the protein(s) encoded by the foreign DNA of the elite event can be done by classical protein detection methods described in the art, such as those based on chromatographic or electromagnetic properties of the protein or the detection by specific monoclonal antibodies (as described in "Guide to protein purification, Murray P. Deutscher editor).

A "kit" as used herein refers to a set of reagents for the purpose of performing the method of the invention, more particularly, the identification of the elite event EE-GH1 in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of EE-GH1 therein. Optionally, the kit can further comprise any other reagent (such as but not limited to hybridizing buffer, label) for identification of EE-GH1 in biological samples, using the specific probe.

The kit of the invention can be used, and its components can be specifically adjusted, for purposes of quality control (e.g., purity of seed lots), detection of the elite event in plant material or material comprising or derived from plant material, such as but not limited to food or feed products.

The present invention relates to the development of an elite event in cotton, EE-GH1, to the plants comprising this event, the progeny obtained from these plants and to the plant cells, or plant material derived from this event. Plants comprising elite event EE-GH1 were obtained through transformation with pGSV71 as described in example 1.

Cotton plants or plant material comprising EE-GH1 can be identified according to the PCR identification protocol described for EE-GH1 in Example 4 herein. Briefly, cotton genomic DNA is amplified by PCR using a primer which specifically recognizes a sequence within the 5' or 3' flanking sequence of EE-GH1, particularly the primer with the sequence of SEQ ID NO: 2, and a primer which recognizes a sequence in the foreign DNA, particularly the primer with the sequence of SEQ ID NO: 3. Endogenous cotton DNA primers are used as controls. If the plant material yields a fragment of between 250 and 290 bp, preferably of about 269 bp, the cotton plant is determined to harbor elite event EE-GH1.

Plants harboring EE-GH1 are characterized by their glufosinate tolerance, which in the context of the present invention includes that plants are tolerant to the herbicide Liberty™. Tolerance to Liberty™ can be tested in different ways. The leaf paint method as described herein, is most useful when you wish to identify both resistant and sensitive plants, but do not want to kill the sensitive ones. Alternatively, tolerance can be tested by Liberty™ spray application. Spray treatments should be made between the leaf stages V3 and V4 for best results. Tolerant plants are characterized by the fact that spraying of the plants with at least 200 grams active ingredient/hectare (g.a.i./ha), preferably 400 g.a.i./ha, and possibly up to 1600 g.a.i./ha (4× the normal field rate), does not kill the plants. A broadcast application should be applied at a rate of 28–34 oz Liberty™. It is best to apply at a volume of 20 gallons of water per acre using a flat fan type nozzle while being careful not to direct spray applications directly into the whorl of the plants to avoid surfactant burn on the leaves. The herbicide effect should appear within 48 hours and be clearly visible within 5–7 days.

Plants harboring EE-GH1 can further be characterized by the presence in their cells of phosphinothricin acetyl transferase as determined by a PAT assay (De Block et al, 1987, supra).

Plants harboring EE-GH1 can, for example, be obtained from seeds deposited at the ATCC under accession number PTA-3343, which contain 50% kernels that are hemizigous for the elite event. Such plants can be further propagated to introduce the elite event of the invention into other cultivars of the same plant species. Selected seeds obtained from these plants contain the elite event stably incorporated into their genome. The invention further relates to plants derived from the ATCC accession number PTA-334, comprising EE-GH1. The term "derived from" herein indicates that the plants are related, i.e. they are both progeny (direct or of two or more generations) of the same transformant by crossing.

Plants harboring EE-GH1 are also characterized by having agronomical characteristics that are comparable to commercially available varieties of cotton in the US, in the absence of weed pressure and use of Liberty™ for weed control. It has been observed that the presence of a foreign DNA in the insertion region of the cotton plant genome described herein, confers particularly interesting phenotypic and molecular characteristics to the plants comprising this event. More specifically, the presence of the foreign DNA in this particular region in the genome of these plants, results in plants which display a stable phenotypic expression of the gene of interest without significantly compromising any aspect of desired agronomic performance of the plants. Thus, the insertion region, corresponding to a sequence comprising the plant DNA of SEQ ID NO: 1 and/or SEQ ID NO: 4, more particularly a sequence corresponding to SEQ ID NO: 5, most particularly the insertion site of EE-GH1 therein, is shown to be particularly suited for the introduction of a gene(s) of interest. More particularly, the insertion region of EE-GH1 (corresponding to a DNA sequence of at least 40 bp in the cotton genome within SEQ ID NO: 5), or a sequence of at least 40 bp which hybridizes under stringent conditions to the complement of the sequence of SEQ ID NO: 5, is particularly suited for the introduction of foreign DNA comprising a herbicide tolerance gene, ensuring expression of each of these genes in the plant without compromising agronomic performance.

A recombinant DNA molecule can be specifically inserted in an insertion region by targeted insertion methods. Such methods are well known to those skilled in the art and comprise, for example, homologous recombination using a recombinase such as, but not limited to the FLP recombinase from *Saccharomyces cerevisiae* (published PCTP application WO 99/25821), the CRE recombinase from *Escherichia*

*coli* phage P1 (published PCT application WO 99/25840), the recombinase from pSR1 of *Saccharomyces rouxii* (Araki et al. 1985, *J Mol Biol* 182:191–203), the Gin/gix system of phage Mu (Maeser and Kahlmann, 1991, Mol Gen Genetics 230:170–176) or the lambda phage recombination system (such as described in U.S. Pat. No. 4,673,640).

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc Nat Acad Sci USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Wisconsin Package (from the Genetics Computer Group, Inc). Sequences are indicated as "essentially similar" when such sequences have a sequence identity of at least about 75%, particularly at least about 80%, more particularly at least about 85%, quite particularly about 90%, especially about 95%, more especially about 100%, quite especially are identical. It is clear that when RNA sequences are said to be essentially similar or have a certain degree of sequence identity with DNA sequences, thymine (T) in the DNA sequence is considered equal to uracil (U) in the RNA sequence. "Complementary to" as used herein refers to the complementarity between the A and T (U), and G and C nucleotides in nucleotide sequences.

As used in herein, a "biological sample" is a sample of a plant, plant material or products comprising plant material. The term "plant" is intended to encompass cotton (such as but not limited to *Gossypium hirsutum*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are preferably tested for the presence of nucleic acids specific for EE-GH1, implying the presence of nucleic acids in the samples. Thus the methods referred to herein for identifying elite event EE-GH1 in biological samples, preferably relate to the identification in biological samples of nucleic acids which comprise the elite event.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The following examples describe the development and characteristics of cotton plants harboring the elite events EE-GH1 as well as the development of tools for the identification of elite event EE-GH1 in biological samples.

Unless otherwise stated, all recombinant DNA techniques are carried out according to standard protocols as described in Sambrook et al. (1989) *Molecular Cloning: A Laboratory Manual*, Second Edition, Cold Spring Harbour Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

In the description and examples, reference is made to the following sequences:

| | |
|---|---|
| SEQ ID NO: 1: | sequence comprising the 5' flanking region |
| SEQ ID NO: 2: | primer GHI06 |
| SEQ ID NO: 3: | primer GHI05 |
| SEQ ID NO: 4: | sequence comprising the 3' flanking region |
| SEQ ID NO: 5: | insertion region |
| SEQ ID NO: 6: | plasmid pGSV71 |
| SEQ ID NO: 7: | plasmid pRVA44 |
| SEQ ID NO: 8: | primer MDB327 |
| SEQ ID NO: 9: | primer MLD015 |
| SEQ ID NO: 10: | primer MLD016 |
| SEQ ID NO: 11: | primer MDB612 |
| SEQ ID NO: 12: | primer MDB053 |
| SEQ ID NO: 13: | primer MDB356 |
| SEQ ID NO: 14: | primer DPA017 |
| SEQ ID NO: 15: | primer MLDO19 |
| SEQ ID NO: 16: | sequence comprising target site deletion |
| SEQ ID NO: 17: | primer GHI01 |
| SEQ ID NO: 18: | primer GHI02 |

EXAMPLES

Example 1

Transformation of Cotton with a Herbicide Tolerance Gene 1.1. Construction of the Chimeric DNA Comprising the Bar Gene Under the Control of a Constitutive Promoter A plasmid pGSV71 was constructed following standard procedures. The sequence of the genetic elements of plasmid pGSV71 is given in table 1 (SEQ ID NO: 6):

TABLE 1

Nucleotide positions of the genetic elements in pGSV71

| Nt positions | Abbreviation | Description and references |
|---|---|---|
| 198–222 | — | Right border Repeat from the TL-DNA from pTiB6S3 (Gielen et al., 1984, EMBO J. 3:835–846) |
| 223–249 | — | Polylinker |
| 250–1634 | P35S3 | Promoter of the 35S RNA of Cauliflower Mosaic Virus (Odell et al., (1985), Nature 313:810–812) |
| 1635–2186 | bar | Coding sequence encoding phosphinothricine-acetyl-transferase from *Streptomyces hygroscopicus* (Thompson et al., (1987) EMBO J. 6: 2519–2523). The N-terminal two codons of the wild-type bar coding |

TABLE 1-continued

Nucleotide positions of the genetic elements in pGSV71

| Nt positions | Abbreviation | Description and references |
|---|---|---|
| | | region have been substituted for codons ATG and GAG respectively. |
| 2187–2205 | — | Polylinker |
| 2206–2465 | 3'nos | A 260 bp TaqI fragment from the 3' untranslated region of the nopaline-synthase gene originating from the T-DNA of pTiT37 (Depicker et al., 1982, J. Mol. Appl. Genet. 1:561–573) |
| 2466–2519 | — | Polylinker |
| 2520–2544 | — | Left border Repeat from the TL-DNA from pTiB6S3 (Gielen et al., 1984, EMBO J. 3:835–846) |

1.2. Transformation of *Gossypium hirsutum*

Cotton tissue from Coker312 plants was transformed with pGSV71 using Agrobacterium transformation (U.S. Pat. No. 5,986,181) and regenerated to plants on appropriate media.

The small plantlets initiated on the selective regeneration media were transferred to new medium for germination (all medium is hormone-free). Plantlets were then transferred to the growth chambers or to the greenhouses.

Selection was done on phosphinothricin (PPT) at all stages except plantlet regeneration, which was done in the absence of PPT to accelerate growth. This resulted in a set of primary transformants (plants of generation T0).

Example 2

Development of Events 2.1. Development of Lines Carrying the Event Trait

T0 shoots were transferred to greenhouse soil and plants were screened for glufosinate tolerance and for the presence of the PAT enzyme with a PAT ELISA (Steffens Biotechnische Analysen GmbH, Ebringen, Germany).

T1 to T3 plants were grown in the greenhouse and tested for Liberty™ tolerance at a 2× rate (by spraying 56 oz/ha). Positive plants were tested for expression of the bar gene using the Pat assay as described by Deblock et al. 1987 (EMBO J. 6:2513–2518).

Presence of the foreign DNA and copy number was checked by Southern blot analysis. Total genomic DNA was isolated from 1 g of leaf tissue according to the CETAB method of Doyle et al. (1987, Phytochem. Bull. 19:11) and digested with EcoRI restriction enzyme.

Probes such as the following were used for Southern analysis:

"bar" probe: 474 bp KpnI-BglII digest of plasmid pDE110 (WO 92/09696)

"35S" probe: 892 bp NcoI-MunI digest of plasmid pRVA44 (SEQ ID NO: 7)

T2 Plants were also evaluated for general phenotypic characteristics compared to the non-transgenic isogenic lines. In later generations, the lines for which no negative penalties on phenotype or agronomic performance was observed for the presence of the transgene either in hemizygous or in homozygous condition, as compared to wild-types were selected.

T4 material was grown in the field and tested under field conditions for Liberty™ tolerance according to different schedules.

In later generations, plants were compared to commercial varieties for yield, fiber quality and plant mapping data. Agronomic characteristics, such as plant height, height to node, boll retention, stand, vigor, fiber length, fiber strength and lint yield were evaluated.

It was determined that one event performed equally or better than the comparable checks and that for this event yield was dependent on background rather than on presence of the transgene.

2.2. Selection of an Elite Event

This selection procedure, yielded one elite event which displayed optimal expression of the 35S-bar gene, i.e. tolerance to glufosinate ammonium, without penalty on agronomic performance and yield. This elite event was named EE-GH1.

2.3. Testing of EE-GH1 in Cotton Varieties with Different Genetic Backgrounds and in Different Locations The selected event was introduced into different commercial genetic backgrounds, including FM989, FM 832, FM958, and FM966 and results of field trials of four different locations were compared. Plants were sprayed with 1600 g.a.i./ha, using different treatments (1×3–5 leaf stage, 4×, 3–5 leaf stage, 1×+1×, 3–5 leaf stage, 4×+4×, 3–5 leaf stage, 0 as control).

Seedling emergence and vigor rating for the elite event was very good.

No visible damage as a result of herbicide application was ever observed after application regardless of rate or stage of development at the time of application.

There were no detrimental effects on morphology or growth habit of plants by herbicide application Furthermore, the event had normal leaf, flower and boll morphology, excellent fertility, and showed no disease or abnormal insect susceptibility in multiple genetic backgrounds. During introgression into multiple genetic backgrounds no aberrant problems or abnormalities were observed over four generations.

2.4. Genetic Analysis of the Locus

The genetic stability of the insert for the EE-GH1 event was checked by molecular and phenotypic analysis in the progeny plants over several generations.

Southern blot analyses of plants of the T1, T2 and T3 generation were compared for the EE-GH1 event. The patterns obtained were found to be identical in the different generations. This proves that the molecular configuration of the foreign DNA in EE-GH1 was stable.

The EE-GH1 event displayed Mendelian segregation for the transgene as a single genetic locus in at least three subsequent generations indicating that the insert is stable.

Example 3

Characterization of Elite Event EE-GH1

3.1 In-Depth Molecular and Genetic Analysis of the Locus

Once the EE-GH1 event was identified as the event in which expression of the transgene as well as overall agronomic performance were optimal, the locus of the transgene was analyzed in detail on a molecular level. This included sequencing of the flanking regions of the transgene.

The sequence of the regions flanking the inserted transgene in the EE-GH1 event was determined using the TAIL-PCR protocol as described by Liu et al. (1995, Plant J. 8(3): 457–463).

a) Determination of the 5' Flanking Region
The primers used were:

| | | Sequence (5'→3') | | Position in pGSV71 |
|---|---|---|---|---|
| Degenerate primer | MDB327 | NTg.Agg.WTC.NWg.TSA.T | (SEQ ID NO:8) | — |
| Primary TAIL | MLD015 | Tgg.TTC.CTA.gCg.TgA.gCC.AgT.g | (SEQ ID NO:9) | 606→585 |
| Second. TAIL | MLD016 | AgC.TgC.TgC.TCT.TgC.CTC.TgT | (SEQ ID NO:10) | 467→447 |
| Tertiary TAIL | GHI05 | ggA.CCg.TTA.TAC.ACA.ACg.Tag | (SEQ ID NO:3) | 358→338 |

Whereby N = A, C, T or g;
S = C or g;
W = A or T

The fragment amplified using MDB327-GHI05 was ca. 1200 bp which was sequenced (5'flank: SEQ ID NO: 1). The sequence between bp 1 and bp 677 comprised plant DNA, while the sequence between bp 678 and bp 850 corresponded to pGSV71 DNA.

b) Determination of the 3' Flanking Region
The primers used were:

| | | Sequence (5'→3') | | Position in pGSV71 |
|---|---|---|---|---|
| Degenerate primer | MDB612 | NgT.gCT.SWg.ANA.WgA.T | (SEQ ID NO:11) | — |
| Primary TAIL | MDB053 | CAT.gAC.gTg.ggT.TCC.Tgg.Cag.C | (SEQ ID NO:12) | 2109–2130 |
| Secondary TAIL | MDB356 | AAT.CCT.gTT.gCC.ggT.CTT.gCg | (SEQ ID NO:13) | 2252–2272 |
| Tertiary TAIL | DPA017 | gAT.TAg.AgT.CCC.gCA.ATT.ATA.C | (SEQ ID NO:14) | 2362–2383 |

Whereby: N = A, C, T or g;
S = C or g;
W = A or T

The fragment amplified using MDB612-DPA017 was ca. 400 bp, the complete sequence of which was determined (SEQ ID NO: 4). The sequence between nucleotide 1 and 179 corresponds to T-DNA, while the sequence between nucleotide 180 and 426 corresponds to plant DNA.

c) Identification of the Target Site Deletion
Using primers corresponding to sequences within the flanking regions of the transgene on the wildtype *Gossypium hirsutum* as a template, the insertion site of the transgene was identified.
The following primers were used:

This yielded a 200 bp fragment (SEQ ID NO: 16) in which bp 85 to 122 corresponds to a target site deletion.

| | | |
|---|---|---|
| 1–677: | 5' flanking region | bp 1 to 677 of SEQ ID NO: 1 |
| 678–714: | target site deletion | bp 85 to 122 of SEQ ID NO: 16 |
| 715–916: | 3' flanking region | bp 180 to 426 of SEQ ID NO: 4 |

3.2. Genetic Analysis of the Locus

The genetic stability of the insert was checked by molecular and phenotypic analysis in the progeny plants over several generations.

Southern blot analyses on glufosinate tolerant plants of EE-GH1 cotton plants of the $T_0$, $T_1$ and $T_2$ generation were compared and were found to be identical. This proves that the molecular configuration of the transgene in EE-GH1 containing plants was stable.

The EE-GH1 event displayed Mendelian segregation for the transgene as a single genetic locus in at least three subsequent generations indicating that the insert is stable.

| | Sequence (5'→3') | Position in 5'flank (SEQ ID NO:1) | Position in 3'flank (SEQ ID NO:4) |
|---|---|---|---|
| GHI06 | TTg.CAC.CAT.CTA.gCT.CAC.TC (SEQ ID NO:2) | 815→795 | — — — — — |
| MLD019 | CAA.gAT.gCg.AgC.AAC.TAT.gT (SE ID NO:15) | — — — — — | 285→266 |

On the basis of the above results EE-GH1 was identified as an elite event.

Example 4

Development of Diagnostic Tools for Identity Control

A EE-GH1 Elite event PCR Identification protocol was developed to identify the presence of EE-GH1 in plants, plant material or biological samples.

EE-GH1 Elite Event Polymerase Chain Reaction Identification Protocol

A test run, with all appropriate controls, has to be performed before attempting to screen unknowns. The presented protocol might require optimization for components that may differ between labs (template DNA preparation, Taq DNA polymerase, quality of the primers, dNTP's, thermocyler, etc.).

A DNA positive control (genomic DNA sample known to contain the transgenic sequences). Successful amplification of this positive control demonstrates that the PCR was run under conditions which allow for the amplification of target sequences.

A wildtype DNA control. This is a PCR in which the template DNA provided is genomic DNA prepared from a non-transgenic plant. When the expected result, no amplification of the transgene PCR product but amplification of the endogenous PCR product, is observed this indicates that there is no detectable transgene background amplification in a genomic DNA sample.

Primers

The following primers, which specifically recognize the transgene and a flanking sequence of EE-GH1 are used:

| Primer | Sequence (5'→3') | | Position in SEQ ID NO: 1 | Target |
|---|---|---|---|---|
| GHI05 | ggA.CCg.TTA.TAC.ACA.ACg.Tag | (SEQ ID NO:3) | 758→738 | pGSV71 sequence |
| GHI06 | TTg.CAC.CAT.CTA.gCT.CAC.TC | (SEQ ID NO:2) | 815→795 | Plant DNA Sequence |

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Template DNA

Template DNA is prepared according to the CTAB method described by Doyle and Doyle (1987, Phytochem. Bull. 19: 11). When using DNA prepared with other methods, a test run utilizing different amounts of template should be done. Usually 50 ng of genomic template DNA yields the best results.

Assigned Positive and Negative Controls

The following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

Primers targeting an endogenous sequence are always included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers used are:

```
GHI01: 5'-AAC.CTA.ggC.TgC.TgA.Agg.    (SEQ ID NO:17)
                              AgC-3'
(Alcohol dehydrogenase gene Acc. NO: AF036569,
1070→1090)

GHI02: 5'-CAA.CTC.CTC.CAg.TCA.TCT.    (SEQ ID NO: 18)
                              CCg-3'
(Alcohol dehydrogenase gene Acc. NO: AF036569,
1515→1495)
```

Amplified Fragments

The expected amplified fragments in the PCR reaction are:

| For primer pair GHI01–GHI02: | 445 bp (endogenous control) |
|---|---|
| For primer pair GHI05–GHI06: | 269 bp (EE-GH1 Elite Event) |

PCR Conditions

The PCR mix for 50 μl reactions contains:

5 μl template DNA
5 μl 10× Amplification Buffer (supplied with Taq polymerase)
1 μl 10 mM dNTP's 0.5 μl GHI01 (10 pmoles/μl)
0.5 μl GHI02 (10 pmoles/μl)
1 μl GHI05 (10 pmoles/μl)
1 μl GHI06 (10 pmoles/μl)
0.2 μl Taq DNA polymerase (5 units/μl)
water up to 50 μl The thermocycling profile to be followed for optimal results is the following:

4 min. at 95° C.
Followed by:
1 min. at 95° C.
1 min. at 57° C.
2 min. at 72° C.
For 5 cycles
Followed by:
30 sec. at 92° C.
30 sec. at 57° C.
1 min. at 72° C.
For 25 cycles
Followed by:
5 minutes at 72° C.

Agarose Gel Analysis

Between 10 and 20 μl of the PCR samples should be applied on a 1.5% agarose gel (Tris-borate buffer) with an appropriate molecular weight marker (e.g. 100 bp ladder PHARMACIA).

Validation of the Results

Data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

Lanes showing visible amounts of the transgenic and endogenous PCR products of the expected sizes, indicate that the corresponding plant from which the genomic template DNA was prepared, has inherited the EE-GH1 elite event. Lanes not showing visible amounts of the transgenic PCR product and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

Use of Discriminating PCR Protocol to Identify EE-GH1

Cotton leaf material from plants comprising different transgenic events (samples 1 to 4) was tested according to the above-described protocol. Samples from cotton wild-type were taken as negative controls.

The results of the PCR analysis are illustrated in FIG. 1. Sample 1 is recognized as comprising elite event EE-GH1. All other tested lines do not comprise this elite event.

Example 5

Introgression of EE-GH1 into Preferred Cultivars

Elite event EE-GH1 is introduced by repeated back-crossing into the following commercial cotton cultivars: FM5013, FM5015, FM5017, FM989, FM832, FM966 and FM958.

It is observed that the introgression of the elite event into these cultivars does not significantly influence any of the desirable phenotypic or agronomic characteristics of these cultivars (no linkage drag) while expression of the transgene, as determined by glufosinate tolerance, meets commercially acceptable levels. This confirms the status of event EE-GH1 as an elite event.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event EE-GH1 was deposited as EE-GH1 at the ATCC (10801 University Blvd., Manassas, Va. 20110-2209) on Apr. 26, 2001, under ATCC accession number PTA-3343.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

The above description of the invention is intended to be illustrative and not limiting. Various changes or modifications in the embodiments described may occur to those skilled in the art. These can be made without departing from the spirit or scope of the invention.

What is claimed is:

1. A transgenic cotton plant or seed, cells or tissues thereof comprising elite event EE-GH1 in its genome, reference seed comprising said event having been deposited at the ATCC under accession number PTA-3343.

2. The transgenic cotton plant, or seed, cells or tissues of claim 1, the genomic DNA of which, when analyzed using the Elite event identification protocol for EE-GH1 with two primers comprising the nucleotide sequence of SEQ ID NO: 2 and SEQ ID NO:3 respectively, yields a DNA fragment of between 250 and 290 bp.

3. The cotton plant, or seed, cells or tissues thereof, according to claim 2, wherein said DNA fragment is a fragment of about 269 bp.

4. A cotton plant, or seed, cells or tissues thereof, each comprising elite event EE-GH1 in its genome, obtained by propagation of and/or breeding with a cotton plant growth from the seed deposited at the ATCC under accession number PTA-3343.

5. A cotton plant, seed, cells or tissues thereof, each comprising elite event EE-GH1 in its genome, which is the progeny of the seed deposited at the ATCC under accession number PTA-3343.

6. A seed deposited at the ATCC under accession number PTA-3343.

7. A cotton seed comprising elite event EE-GH1, reference seed comprising said event having been deposited at the ATCC under accession number PTA-3343.

8. A transgenic cotton plant, cell or tissue comprising elite event EE-GH1, produced from the seed of claim 7.

9. A transgenic cotton plant, seed, cells or tissues thereof, each comprising elite event EE-GH1 in its genome, which is the progeny of the cotton plant of claim 1.

10. A transgenic cotton plant, seed, cells or tissues thereof, each comprising elite event EE-GH1 in its genome, which is the progeny of the cotton plant of claim 8.

* * * * *

SEQUENCE LISTING

<160> NUMBER OF SEQ ID NOS: 18

<210> SEQ ID NO 1
<211> LENGTH: 850
<212> TYPE: DNA
<213> ORGANISM: Artificial Sequence
<220> FEATURE:
<223> OTHER INFORMATION: sequence comprising 5' flanking region -continued

```
<400> SEQUENCE: 1 aaagggatg  agattgaatg  ttaccttatc  aacaaaagga  gttgtagctc  atggaacaac     60
aatagtcttt  tccacggaaa  cctagatgat  gtttctccaa  tgcttgataa  atctttaaca   120
ttgtcatcat  aagttgcaac  ctcatgtttc  acacaagcat  caatcaaatg  ttgatcttca   180
ttactaaaat  gtgcttgatc  cttccttaca  caaatctacc  tatgttgtgg  tattttgttc   240
tattcatcat  tctaacaagt  tttgcaattg  agttgaactt  cttccaatct  cgtatcagcc   300
tataatagtg  gggtctaata  tgtccatttt  tcccacaata  atgacatata  atctttctaa   360
agcttttatt  ctctgcctta  tgatgaaaag  aacccaaatc  tttaacttta  acaaaaataa   420
gatgagcgat  aggttcttca  cctttattga  tgtaaccaag  tcctctatgg  catggttcaa   480
ttctcattga  agccaaaatt  tcatgaaact  tctcacattg  gcctctaaac  ttcttcaaga   540
tagcctttgc  accatctagc  tcactcttgg  ttgttttcaa  aacatcatcc  gtttcttgga   600
ccacaatttt  gagcttttca  ttttctattt  tgaggataat  agtttattcc  ctcaaggaac   660
tattcaactg  agcttaacag  tactcggccg  tcgaccgcgg  tacccggaat  ccaatccca    720 caaaaatctg  agcttaacag  cacagttgct  cctctcagag  cagaatcggg  tattcaacac   780
cctcatatca  actactacgt  tgtgtataac  ggtccacatg  ccggtatata  cgatgactgg   840
ggttgtacaa                                                               850

<210> SEQ ID NO 2
<211> LENGTH: 20
<212> TYPE: DNA
<213> ORGANISM: Artificial Sequence
<220> FEATURE:
<223> OTHER INFORMATION: primer GHI06

<400> SEQUENCE: 2
ttgcaccatc  tagctcactc                                                    20

<210> SEQ ID NO 3
<211> LENGTH: 21
<212> TYPE: DNA
<213> ORGANISM: Artificial Sequence
<220> FEATURE:
<223> OTHER INFORMATION: primer GHI05

<400> SEQUENCE: 3
ggaccgttat  acacaacgta  g                                                 21

<210> SEQ ID NO 4
<211> LENGTH: 426
<212> TYPE: DNA
<213> ORGANISM: Artificial Sequence
<220> FEATURE:
<223> OTHER INFORMATION: sequence comprising 3' flanking region

<400> SEQUENCE: 4
gattagagtc  ccgcaattat  acatttaata  cgcgatagaa  acaaaatat  agcgcgcaaa     60 ctaggataaa  ttatcgcgcg  cggtgtcatc  tatgttacta  gatcgggaag  atcctctaga   120
gtcgacctgc  aggcatgcaa  gcttagatcc  atggagccat  ttacaattga  atatatcctc   180
caaatattta  aaaagaatat  caccattatc  cgaatcttct  ttaaaatctg  ttagaacacg   240
gtttggaata  gtggtagtaa  aagtaacata  gttgctcgca  tcttgatcta  cattaaactt   300
tcttcatcac  tccaagtgat  tgtaaatgac  ttctatttct  tcttagtatt  agcacattct   360
aattttaagt  gaaacaatcc  cttacattca  taacattgaa  tatccttcta  tcatctcaca   420
``` gcacga 426

<210> SEQ ID NO 5
<211> LENGTH: 961
<212> TYPE: DNA
<213> ORGANISM: Artificial Sequence
<220> FEATURE:
<223> OTHER INFORMATION: sequence comprising insertion region

<400> SEQUENCE: 5

```
aaagggatg agattgaatg ttaccttatc aacaaaagga gttgtagctc atggaacaac        60
aatagtcttt tccacggaaa cctagatgat gtttctccaa tgcttgataa atctttaaca       120
ttgtcatcat aagttgcaac ctcatgtttc acacaagcat caatcaaatg ttgatcttca       180
ttactaaaat gtgcttgatc cttccttaca caaatctacc tatgttgtgg tattttgttc       240
tattcatcat tctaacaagt tttgcaattg agttgaactt cttccaatct cgtatcagcc       300
tataatagtg gggtctaata tgtccatttt tcccacaata atgacatata atctttctaa       360
agcttttatt ctctgcctta tgatgaaaag aacccaaatc tttaacttta acaaaaataa       420
gatgagcgat aggttcttca cctttattga tgtaaccaag tcctctatgg catggttcaa       480
ttctcattga agccaaaatt tcatgaaact ctctcacattg gcctctaaac ttcttcaaga      540
tagcctttgc accatctagc tcactcttgg ttgttttcaa acatcatcc gtttcttgga        600
ccacaatttt gagcttttca ttttctattt tgaggataat agtttattcc ctcaaggaac       660
tattcaactg agcttaaatc tcaattttt ttaacatatg actataagta tcctccaaat        720
atttaaaaag aatatcacca ttatccgaat cttctttaaa atctgttaga acacggtttg       780
gaatagtggt agtaaaagta acatagttgc tcgcatcttg atctacatta aactttcttc       840
atcactccaa gtgattgtaa atgacttcta ttcttctta gtattagcac attctaattt        900
taagtgaaac atcccttac attcataaca ttgaatatcc ttctatcatc tcacagcacg        960
a                                                                      961
```

<210> SEQ ID NO 6
<211> LENGTH: 9555
<212> TYPE: DNA
<213> ORGANISM: Artificial Sequence
<220> FEATURE:
<223> OTHER INFORMATION: plasmid pGSV71

<400> SEQUENCE: 6

```
agattcgaag ctcggtcccg tgggtgttct gtcgtctcgt tgtacaacga aatccattcc        60
cattccgcgc tcaagatggc ttcccctcgg cagttcatca gggctaaatc aatctagccg       120
acttgtccgg tgaaatgggc tgcactccaa cagaaacaat caaacaaaca tacacagcga       180
cttattcaca cgcgacaaat tacaacggta tatatcctgc cagtactcgg ccgtcgaccg       240
cggtacccgg aattccaatc ccacaaaaat ctgagcttaa cagcacagtt gctcctctca       300
gagcagaatc gggtattcaa caccctcata tcaactacta cgttgtgtat aacggtccac       360
atgccggtat atacgatgac tggggttgta caaaggcggc aacaaacggc gttcccggag       420
ttgcacacaa gaaatttgcc actattacag aggcaagagc agcagctgac gcgtacacaa       480
caagtcagca aacagacagg ttgaacttca tccccaaagg agaagctcaa ctcaagccca       540
agagctttgc taaggcccta acaagcccac caaagcaaaa agcccactgg ctcacgctag       600
gaaccaaaag gcccagcagt gatccagccc caaaagagat ctcctttgcc ccggagatta       660
```

-continued

| | |
|---|---|
| caatggacga tttcctctat ctttacgatc taggaaggaa gttcgaaggt gaaggtgacg | 720 |
| acactatgtt caccactgat aatgagaagg ttagcctctt caatttcaga aagaatgctg | 780 |
| acccacagat ggttagagag gcctacgcag caggtctcat caagacgatc tacccgagta | 840 |
| acaatctcca ggagatcaaa taccttccca agaaggttaa agatgcagtc aaaagattca | 900 |
| ggactaattg catcaagaac acagagaaag acatatttct caagatcaga agtactattc | 960 |
| cagtatggac gattcaaggc ttgcttcata accaaggca agtaatagag attggagtct | 1020 |
| ctaaaaaggt agttcctact gaatctaagg ccatgcatgg agtctaagat tcaaatcgag | 1080 |
| gatctaacag aactcgccgt gaagactggc gaacagttca tacagagtct tttacgactc | 1140 |
| aatgacaaga agaaaatctt cgtcaacatg gtggagcacg acactctggt ctactccaaa | 1200 |
| aatgtcaaag atacagtctc agaagaccaa agggctattg agacttttca acaaggata | 1260 |
| atttcgggaa acctcctcgg attccattgc ccagctatct gtcacttcat cgaaaggaca | 1320 |
| gtagaaaagg aaggtggctc ctacaaatgc catcattgcg ataaaggaaa ggctatcatt | 1380 |
| caagatgcct ctgccgacag tggtcccaaa gatggacccc cacccacgag gagcatcgtg | 1440 |
| gaaaaagaag acgttccaac cacgtcttca agcaagtgg attgatgtga catctccact | 1500 |
| gacgtaaggg atgacgcaca atcccactat ccttcgcaag acccttcctc tatataagga | 1560 |
| agttcatttc atttggagag gacacgctga aatcaccagt ctctctctat aaatctatct | 1620 |
| ctctctctat aaccatggac ccagaacgac gcccggccga catccgccgt gccaccgagg | 1680 |
| cggacatgcc ggcggtctgc accatcgtca accactacat cgagacaagc acggtcaact | 1740 |
| tccgtaccga gccgcaggaa ccgcaggagt ggacggacga cctcgtccgt ctgcgggagc | 1800 |
| gctatccctg gctcgtcgcc gaggtggacg gcgaggtcgc cggcatcgcc tacgcgggcc | 1860 |
| cctggaaggc acgcaacgcc tacgactgga cggccgagtc gaccgtgtac gtctcccccc | 1920 |
| gccaccagcg gacgggactg ggctccacgc tctacaccca cctgctgaag tccctggagg | 1980 |
| cacagggctt caagagcgtg gtcgctgtca tcgggctgcc caacgacccg agcgtgcgca | 2040 |
| tgcacgaggc gctcggatat gcccccccgcg gcatgctgcg ggcggccggc ttcaagcacg | 2100 |
| ggaactggca tgacgtgggt ttctggcagc tggacttcag cctgccggta ccgccccgtc | 2160 |
| cggtcctgcc cgtcaccgag atctgagatc acgcgttcta ggatccgaag cagatcgttc | 2220 |
| aaacatttgg caataaagtt tcttaagatt gaatcctgtt gccggtcttg cgatgattat | 2280 |
| catataattt ctgttgaatt acgttaagca tgtaataatt aacatgtaat gcatgacgtt | 2340 |
| atttatgaga tgggttttta tgattagagt cccgcaatta tacatttaat acgcgataga | 2400 |
| aaacaaaata tagcgcgcaa actaggataa attatcgcgc gcggtgtcat ctatgttact | 2460 |
| agatcgggaa gatcctctag agtcgacctg caggcatgca agcttagatc catggagcca | 2520 |
| tttacaattg aatatatcct gccgccgctg ccgctttgca cccggtggag cttgcatgtt | 2580 |
| ggtttctacg cagaactgag ccggttaggc agataaattc cattgagaac tgagccatgt | 2640 |
| gcaccttccc cccaacacgg tgagcgacgg ggcaacggag tgatccacat gggactttta | 2700 |
| aacatcatcc gtcggatggc gttgcgagag aagcagtcga tccgtgagat cagccgacgc | 2760 |
| accgggcagg cgcgcaacac gatcgcaaag tatttgaacg caggtacaat cgagccgacg | 2820 |
| ttcacggtac cggaacgacc aagcaagcta gcttagtaaa gccctcgcta gattttaatg | 2880 |
| cggatgttgc gattacttcg ccaactattg cgataacaag aaaaagccag cctttcatga | 2940 |
| tatatctccc aatttgtgta gggcttatta tgcacgctta aaaataataa agcagactt | 3000 |
| gacctgatag tttggctgtg agcaattatg tgcttagtgc atctaacgct tgagttaagc | 3060 |

```
cgcgccgcga agcggcgtcg gcttgaacga attgttagac attatttgcc gactaccttg   3120
gtgatctcgc ctttcacgta gtggacaaat tcttccaact gatctgcgcg cgaggccaag   3180
cgatcttctt cttgtccaag ataagcctgt ctagcttcaa gtatgacggg ctgatactgg   3240
gccggcaggc gctccattgc ccagtcggca gcgacatcct tcggcgcgat tttgccggtt   3300
actgcgctgt accaaatgcg ggacaacgta agcactacat ttcgctcatc gccagcccag   3360
tcgggcggcg agttccatag cgttaaggtt tcatttagcg cctcaaatag atcctgttca   3420
ggaaccggat caaagagttc ctccgccgct ggacctacca aggcaacgct atgttctctt   3480
gcttttgtca gcaagatagc cagatcaatg tcgatcgtgg ctggctcgaa gatacctgca   3540
agaatgtcat tgcgctgcca ttctccaaat tgcagttcgc gcttagctgg ataacgccac   3600
ggaatgatgt cgtcgtgcac aacaatggtg acttctacag cgcggagaat ctcgctctct   3660
ccaggggaag ccgaagtttc caaaaggtcg ttgatcaaag ctcgccgcgt tgtttcatca   3720
agccttacgg tcaccgtaac cagcaaatca atatcactgt gtggcttcag gccgccatcc   3780
actgcggagc cgtacaaatg tacgccagc aacgtcggtt cgagatggcg ctcgatgacg   3840
ccaactacct ctgatagttg agtcgatact tcggcgatca ccgcttccct catgatgttt   3900
aactttgttt tagggcgact gccctgctgc gtaacatcgt tgctgctcca taacatcaaa   3960
catcgaccca cggcgtaacg cgcttgctgc ttggatgccc gaggcataga ctgtacccca   4020
aaaaaacagt cataacaagc catgaaaacc gccactgcgc cgttaccacc gctgcgttcg   4080
gtcaaggttc tggaccagtt gcgtgagcgc atacgctact tgcattacag cttacgaacc   4140
gaacaggctt atgtccactg ggttcgtgcc ttcatccgtt tccacggtgt gcgtcacccg   4200
gcaaccttgg gcagcagcga agtcgaggca tttctgtcct ggctggcgaa cgagcgcaag   4260
gtttcggtct ccacgcatcg tcaggcattg gcggccttgc tgttcttcta cggcaagtgc   4320
tgtgcacgga tctgccctgg cttcaggaga tcggaagacc tcggccgtcc gggcgcttgc   4380
cggtggtgct gaccccggat gaagtggttc gcatcctcgg ttttctggaa ggcgagcatc   4440
gtttgttcgc ccagcttctg tatggaacgg gcatgcggat cagtgagggt ttgcaactgc   4500
gggtcaagga tctggatttc gatcacggca cgatcatcgt gcgggagggc aagggctcca   4560
aggatcgggc cttgatgtta cccgagagct tggcacccag cctgcgcgag cagggatcga   4620
tccaacccct ccgctgctat agtgcagtcg gcttctgacg ttcagtgcag ccgtcttctg   4680
aaaacgacat gtcgcacaag tcctaagtta cgcgacaggc tgccgccctg ccctttttcct  4740
ggcgttttct tgtcgcgtgt tttagtcgca taaagtagaa tacttgcgac tagaaccgga   4800
gacattacgc catgaacaag agcgccgccg ctggcctgct gggctatgcc cgcgtcagca   4860
ccgacgacca ggacttgacc aaccaacggg ccgaactgca cgcggccggc tgcaccaagc   4920
tgttttccga gaagatcacc ggcaccaggc gcgaccgccc ggagctggcc aggatgcttg   4980
accacctacg ccctggcgac gttgtgacag tgaccaggct agaccgcctg gcccgcagca   5040
cccgcgacct actggacatt gccgagcgca tccaggaggc cggcgcgggc ctgcgtagcc   5100
tggcagagcc gtgggccgac accaccacgc cggccggccg catggtgttg accgtgttcg   5160
ccggcattgc cgagttcgag cgttccctaa tcatcgaccg cacccggagc gggcgcgagg   5220
ccgccaaggc ccgaggcgtg aagtttggcc cccgccctac cctcaccccg gcacagatcg   5280
cgcacgcccg cgagctgatc gaccaggaag gccgcaccgt gaaagaggcg gctgcactgc   5340
ttggcgtgca tcgctcgacc ctgtaccgcg cacttgagcg cagcgaggaa gtgacgccca   5400
```

-continued

```
ccgaggccag gcggcgcggt gccttccgtg aggacgcatt gaccgaggcc gacgccctgg    5460
cggccgccga gaatgaacgc caagaggaac aagcatgaaa ccgcaccagg acggccagga    5520
cgaaccgttt ttcattaccg aagagatcga ggcggagatg atcgcggccg ggtacgtgtt    5580
cgagccgccc gcgcacgtct caaccgtgcg gctgcatgaa atcctggccg gtttgtctga    5640
tgccaagctg gcggcctggc cggccagctt ggccgctgaa gaaaccgagc gccgccgtct    5700
aaaaaggtga tgtgtatttg agtaaaacag cttgcgtcat gcggtcgctg cgtatatgat    5760
gcgatgagta aataaacaaa tacgcaaggg gaacgcatga aggttatcgc tgtacttaac    5820
cagaaaggcg ggtcaggcaa gacgaccatc gcaacccatc tagcccgcgc cctgcaactc    5880
gccggggccg atgttctgtt agtcgattcc gatccccagg gcagtgcccg cgattgggcg    5940
gccgtgcggg aagatcaacc gctaaccgtt gtcggcatcg accgcccgac gattgaccgc    6000
gacgtgaagg ccatcggccg gcgcgacttc gtagtgatcg acggagcgcc ccaggcggcg    6060
gacttggctg tgtccgcgat caaggcagcc gacttcgtgc tgattccggt gcagccaagc    6120
ccttacgaca tatgggccac cgccgacctg gtggagctgg ttaagcagcg cattgaggtc    6180
acggatggaa ggctacaagc ggcctttgtc gtgtcgcggg cgatcaaagg cacgcgcatc    6240
ggcggtgagg ttgccgaggc gctggccggg tacgagctgc ccattcttga gtcccgtatc    6300
acgcagcgcg tgagctaccc aggcactgcc gccgccggca caaccgttct tgaatcagaa    6360
cccgagggcg acgctgcccg cgaggtccag gcgctggccg ctgaaattaa atcaaaactc    6420
atttgagtta atgaggtaaa gagaaaatga gcaaaagcac aaacacgcta agtgccggcc    6480
gtccgagcgc acgcagcagc aaggctgcaa cgttggccag cctggcagac acgccagcca    6540
tgaagcgggt caactttcag ttgccggcgg aggatcacac caagctgaag atgtacgcgg    6600
tacgccaagg caagaccatt accgagctgc tatctgaata catcgcgcag ctaccagagt    6660
aaatgagcaa atgaataaat gagtagatga attttagcgg ctaaaggagg cggcatggaa    6720
aatcaagaac aaccaggcac cgacgccgtg gaatgcccca tgtgtggagg aacgggcggt    6780
tggccaggcg taagcggctg ggttgtctgc cggccctgca atggcactgg aacccccaag    6840
cccgaggaat cggcgtgacg gtcgcaaacc atccggcccg gtacaaatcg cgcggcgct    6900 gggtgatgac ctggtggaga agttgaaggc cgcgcaggcc gcccagcggc aacgcatcga    6960
ggcagaagca cgccccggtg aatcgtggca agcggccgct gatcgaatcc gcaaagaatc    7020
ccggcaaccg ccggcagccg gtgcgccgtc gattaggaag ccgcccaagg gcgacgagca    7080
accagatttt ttcgttccga tgctctatga cgtgggcacc cgcgatagtc gcagcatcat    7140
ggacgtggcc gttttccgtc tgtcgaagcg tgaccgacga gctggcgagg tgatccgcta    7200
cgagcttcca gacgggcacg tagaggtttc gcagggccg gccggcatgg ccagtgtgtg    7260
ggattacgac ctggtactga tggcggtttc ccatctaacc gaatccatga accgataccg    7320
ggaagggaag ggagacaagc ccggccgcgt gttccgtcca cacgttgcgg acgtactcaa    7380
gttctgccgg cgagccgatg gcggaaagca gaaagacgac ctggtagaaa cctgcattcg    7440
gttaaacacc acgcacgttg ccatgcagcg tacgaagaag gccaagaacg gccgcctggt    7500
gacggtatcc gagggtgaag ccttgattag ccgctacaag atcgtaaaga gcgaaaccgg    7560
gcggccggag tacatcgaga tcgagctagc tgattggatg taccgcgaga tcacagaagg    7620
caagaacccg gacgtgctga cggttcaccc cgattacttt ttgatcgatc cggcatcgg    7680 ccgttttctc taccgcctgg cacgccgcgc cgcaggcaag gcagaagcca gatggttgtt    7740
caagacgatc tacgaacgca gtggcagcgc cggagagttc aagaagttct gtttcaccgt    7800
```

-continued

```
gcgcaagctg atcgggtcaa atgacctgcc ggagtacgat ttgaaggagg aggcggggca      7860
ggctggcccg atcctagtca tgcgctaccg caacctgatc gagggcgaag catccgccgg      7920
ttcctaatgt acggagcaga tgctagggca aattgcccta gcaggggaaa aggtcgaaa       7980 aggtctcttt cctgtggata gcacgtacat tgggaaccca agccgtaca ttgggaaccg       8040 gaacccgtac attgggaacc caaagccgta cattgggaac cggtcacaca tgtaagtgac      8100
tgatataaaa gagaaaaaag gcgattttc cgcctaaaac tctttaaaac ttattaaaac       8160
tcttaaaacc cgcctggcct gtgcataact gtctggccag cgcacagccg aagagctgca      8220
aaaagcgcct acccttcggt cgctgcgctc cctacgcccc gccgcttcgc gtcggcctat      8280
cgcggccgct ggccgctcaa aaatggctgg cctacggcca gcaatctac cagggcgcgg       8340 acaagccgcg ccgtcgccac tcgaccgccg gcgcccacat caaggcaccc tgcctcgcgc      8400
gtttcggtga tgacggtgaa aacctctgac acatgcagct cccggagacg gtcacagctt      8460
gtctgtaagc ggatgccggg agcagacaag cccgtcaggg cgcgtcagcg ggtgttggcg      8520
ggtgtcgggg cgcagccatg acccactcac gtagcgatag cggagtgtat actggcttaa      8580
ctatgcggca tcagagcaga ttgtactgag agtgcaccat atgcggtgtg aaataccgca      8640
cagatgcgta aggagaaaat accgcatcag gcgctcttcc gcttcctcgc tcactgactc      8700
gctgcgctcg gtcgttcggc tgcggcgagc ggtatcagct cactcaaagg cggtaatacg      8760
gttatccaca gaatcagggg ataacgcagg aaagaacatg tgagcaaaag gccagcaaaa      8820
ggccaggaac cgtaaaaagg ccgcgttgct ggcgtttttc cataggctcc gcccccctga      8880
cgagcatcac aaaaatcgac gctcaagtca gaggtggcga aacccgacag gactataaag      8940
ataccaggcg tttccccctg gaagctccct cgtgcgctct cctgttccga ccctgccgct      9000
taccggatac ctgtccgcct ttctcccttc gggaagcgtg gcgctttctc atagctcacg      9060
ctgtaggtat ctcagttcgg tgtaggtcgt tcgctccaag ctgggctgtg tgcacgaacc      9120
ccccgttcag cccgaccgct gcgccttatc cggtaactat cgtcttgagt ccaacccggt      9180
aagacacgac ttatcgccac tggcagcagc cactggtaac aggattagca gagcgaggta      9240
tgtaggcggt gctacagagt tcttgaagtg gtggcctaac tacggctaca ctagaaggac      9300
agtatttggt atctgcgctc tgctgaagcc agttaccttc ggaaaaagag ttggtagctc      9360
ttgatccggc aaacaaacca ccgctggtag cggtggtttt tttgtttgca agcagcagat      9420
tacgcgcaga aaaaaggat ctcaagaaga tccggaaaac gcaagcgcaa agagaaagca       9480
ggtagcttgc agtgggctta catggcgata gctagactgg gcggttttat ggacagcaag      9540
cgaaccggaa ttgcc                                                       9555
```

<210> SEQ ID NO 7
<211> LENGTH: 4182
<212> TYPE: DNA
<213> ORGANISM: Artificial Sequence
<220> FEATURE:
<223> OTHER INFORMATION: plasmid pRVA44

<400> SEQUENCE: 7

```
tcgcgcgttt cggtgatgac ggtgaaaacc tctgacacat gcagctcccg gagacggtca       60
cagcttgtct gtaagcggat gccggagca gacaagcccg tcagggcgcg tcagcgggtg       120
ttggcgggtg tcgggctgg cttaactatg cggcatcaga gcagattgta ctgagagtgc       180
accatacctg caggcaattg gtacctacgt atgcatggcg cgccatatgc ccgggccctg      240
```

-continued

```
tacagcggcc gcgttcctac gcagcaggtc tcatcaagac gatctacccg agtaacaatc    300
tccaggagat caaatacctt cccaagaagg ttaaagatga agtcaaaaga ttcaggacta    360
attgcatcaa gaacacagag aaagacatat ttctcaagat cagaagtact attccagtat    420
ggacgattca aggcttgctt cataaaccaa ggcaagtaat agagattgga gtctctaaaa    480
aggtagttcc tactgaatct aaggccatgc atggagtcta agattcaaat cgaggatcta    540
acagaactcg ccgtgaagac tggcgaacag ttcatacaga gtcttttacg actcaatgac    600
aagaagaaaa tcttcgtcaa catggtggag cacgacactc tggtctactc caaaaatgtc    660
aaagatacag tctcagaaga ccaaaggggct attgagactt tcaacaaag gataatttcg    720
ggaaacctcc tcggattcca ttgcccagct atctgtcact tcatcgaaag gacagtagaa    780
aaggaaggtg gctcctacaa atgccatcat tgcgataaag gaaaggctat cattcaagat    840
gcctctgccg acagtggtcc caaagatgga cccccaccca cgaggagcat cgtggaaaaa    900
gaagacgttc caaccacgtc ttcaaagcaa gtggattgat gtgacatctc cactgacgta    960
agggatgacg cacaatccca ctatccttcg caagacccctt cctctatata aggaagttca   1020
tttcatttgg agaggacacg ctgaaatcac cagtctctct ctataaatct atctctctct   1080
ctataaccat ggacccagaa cgacgcccgg ccgacatccg ccgtgccacc gaggcggaca   1140
tgccggcggt ctgcaccatc gtcaaccact acatcgagac aagcacggtc aacttccgta   1200
ccgagccgca ggaaccgcag gagtggacgg acgacctcgt ccgtctgcgg gagcgctatc   1260
cctggctcgt cgccgaggtg gacggcgagg tcgccggcat cgcctacgcg ggcccctgga   1320
aggcacgcaa cgcctacgac tggacggccg agtcgaccgt gtacgtctcc ccccgccacc   1380
agcggacggg actgggctcc acgtctctaca cccacctgct gaagtccctg gaggcacagg   1440
gcttcaagag cgtggtcgct gtcatcgggc tgcccaacga cccgagcgtg cgcatgcacg   1500
aggcgctcgg atatgccccc cgcggcatgc tgcgggcggc cggcttcaag cacgggaact   1560
ggcatgacgt gggtttctgg cagctggact tcagcctgcc ggtaccgccc cgtccggtcc   1620
tgcccgtcac cgagatctga tctcacgcgt ctaggatccg aagcagatcg ttcaaacatt   1680
tggcaataaa gtttcttaag attgaatcct gttgccggtc ttgcgatgat tatcatataa   1740
tttctgttga attacgttaa gcatgtaata attaacatgt aatgcatgac gttatttatg   1800
agatgggttt ttatgattag agtcccgcaa ttatacattt aatacgcgat agaaaacaaa   1860
atatagcgcg caaactagga taaattatcg cgcgcggtgt catctatgtt actagatcgg   1920
gaagatcctc tagagcgatc gcaagcttgg cgtaatcatg gtcatagctg tttcctgtgt   1980
gaaattgtta tccgctcaca attccacaca acatacgagc cggaagcata agtgtaaag    2040
cctggggtgc ctaatgagtg agctaactca cattaattgc gttgcgctca ctgcccgctt   2100
tccagtcggg aaacctgtcg tgccagctgc attaatgaat cggccaacgc gcgggagag    2160
gcggtttgcg tattgggcgc tcttccgctt cctcgctcac tgactcgctg cgctcggtcg   2220
ttcggctgcg gcgagcggta tcagctcact caaaggcggt aatacggtta ccacagaat    2280
caggggataa cgcaggaaag aacatgtgag caaaaggcca gcaaaggcc aggaaccgta    2340
aaaaggccgc gttgctggcg ttttttccata ggctccgccc ccctgacgag catcacaaaa   2400
atcgacgctc aagtcagagg tggcgaaacc cgacaggact ataaagatac caggcgttc    2460
ccccctggaag ctccctcgtg cgctctcctg ttccgaccct gccgcttacc ggatacctgt   2520
ccgcctttct cccttcggga agcgtggcgc tttctcaaag ctcacgctgt aggtatctca   2580
gttcggtgta ggtcgttcgc tccaagctgg gctgtgtgca cgaacccccc gttcagcccg   2640
```

```
accgctgcgc cttatccggt aactatcgtc ttgagtccaa cccggtaaga cacgacttat    2700
cgccactggc agcagccact ggtaacagga ttagcagagc gaggtatgta ggcggtgcta    2760
cagagttctt gaagtggtgg cctaactacg gctacactag aagaacagta tttggtatct    2820
gcgctctgct gaagccagtt accttcggaa aaagagttgg tagctcttga tccggcaaac    2880
aaaccaccgc tggtagcggt ggttttttg tttgcaagca gcagattacg cgcagaaaaa    2940
aaggatctca agaagatcct ttgatctttt ctacgggtc tgacgctcag tggaacgaaa    3000
actcacgtta agggattttg gtcatgagat tatcaaaaag gatcttcacc tagatccttt    3060
taaattaaaa atgaagtttt aaatcaatct aaagtatata tgagtaaact tggtctgaca    3120
gttaccaatg cttaatcagt gaggcaccta tctcagcgat ctgtctattt cgttcatcca    3180
tagttgcctg actccccgtc gtgtagataa ctacgatacg ggagggctta ccatctggcc    3240
ccagtgctgc aatgataccg cgagacccac gctcaccggc tccagattta tcagcaataa    3300
accagccagc cggaagggcc gagcgcagaa gtggtcctgc aactttatcc gcctccatcc    3360
agtctattaa ttgttgccgg gaagctagag taagtagttc gccagttaat agtttgcgca    3420
acgttgttgc cattgctaca ggcatcgtgg tgtcacgctc gtcgtttggt atggcttcat    3480
tcagctccgg ttcccaacga tcaaggcgag ttacatgatc ccccatgttg tgcaaaaaag    3540
cggttagctc cttcggtcct ccgatcgttg tcagaagtaa gttggccgca gtgttatcac    3600
tcatggttat ggcagcactg cataattctc ttactgtcat gccatccgta agatgctttt    3660
ctgtgactgg tgagtactca accaagtcat tctgagaata gtgtatgcgg cgaccgagtt    3720
gctcttgccc ggcgtcaata cgggataata ccgcgccaca tagcagaact ttaaaagtgc    3780
tcatcattgg aaaacgttct cggggcgaaa actctcaag gatcttaccg ctgttgagat    3840
ccagttcgat gtaacccact cgtgcaccca actgatcttc agcatctttt actttcacca    3900
gcgtttctgg gtgagcaaaa acaggaaggc aaaatgccgc aaaaaaggga ataagggcga    3960
cacggaaatg ttgaatactc atactcttcc tttttcaata ttattgaagc atttatcagg    4020
gttattgtct catgagcgga tacatatttg aatgtattta gaaaaataaa caaatagggg    4080
ttccgcgcac atttccccga aaagtgccac ctgacgtcta agaaaccatt attatcatga    4140
cattaaccta taaaaatagg cgtatcacga ggccctttcg tc                       4182
```

<210> SEQ ID NO 8
<211> LENGTH: 16
<212> TYPE: DNA
<213> ORGANISM: Artificial Sequence
<220> FEATURE:
<223> OTHER INFORMATION: primer MDB327
<220> FEATURE:
<221> NAME/KEY: misc_feature
<222> LOCATION: (1)..(1)
<223> OTHER INFORMATION: "n" = a, t, c or g
<220> FEATURE:
<221> NAME/KEY: misc_feature
<222> LOCATION: (7)..(7)
<223> OTHER INFORMATION: "w" = a or t
<220> FEATURE:
<221> NAME/KEY: misc_feature
<222> LOCATION: (10)..(10)
<223> OTHER INFORMATION: "n" = a, t, c or g
<220> FEATURE:
<221> NAME/KEY: misc_feature
<222> LOCATION: (11)..(11)
<223> OTHER INFORMATION: "w" = a or t
<220> FEATURE:
<221> NAME/KEY: misc_feature
<222> LOCATION: (14)..(14)

```
<223> OTHER INFORMATION: "s" = g or c

<400> SEQUENCE: 8
ntgaggwtcn wgtsat                                                    16

<210> SEQ ID NO 9
<211> LENGTH: 22
<212> TYPE: DNA
<213> ORGANISM: Artificial Sequence
<220> FEATURE:
<223> OTHER INFORMATION: primer MLD015

<400> SEQUENCE: 9
tggttcctag cgtgagccag tg                                             22

<210> SEQ ID NO 10
<211> LENGTH: 21
<212> TYPE: DNA
<213> ORGANISM: Artificial Sequence
<220> FEATURE:
<223> OTHER INFORMATION: primer MLD016

<400> SEQUENCE: 10
agctgctgct cttgcctctg t                                              21

<210> SEQ ID NO 11
<211> LENGTH: 16
<212> TYPE: DNA
<213> ORGANISM: Artificial Sequence
<220> FEATURE:
<223> OTHER INFORMATION: primer MDB612
<220> FEATURE:
<221> NAME/KEY: misc_feature
<222> LOCATION: (1)..(1)
<223> OTHER INFORMATION: "n" = a, t, c or g
<220> FEATURE:
<221> NAME/KEY: misc_feature
<222> LOCATION: (7)..(7)
<223> OTHER INFORMATION: "s" = c or g
<220> FEATURE:
<221> NAME/KEY: misc_feature
<222> LOCATION: (8)..(8)
<223> OTHER INFORMATION: "w" = a or t
<220> FEATURE:
<221> NAME/KEY: misc_feature
<222> LOCATION: (11)..(11)
<223> OTHER INFORMATION: "n" = a, t, c or g
<220> FEATURE:
<221> NAME/KEY: misc_feature
<222> LOCATION: (13)..(13)
<223> OTHER INFORMATION: "w" = a or t

<400> SEQUENCE: 11
ngtgctswga nawgat                                                    16

<210> SEQ ID NO 12
<211> LENGTH: 22
<212> TYPE: DNA
<213> ORGANISM: Artificial Sequence
<220> FEATURE:
<223> OTHER INFORMATION: primer MDB053

<400> SEQUENCE: 12
catgacgtgg gtttctggca gc                                             22

<210> SEQ ID NO 13
<211> LENGTH: 21
<212> TYPE: DNA
<213> ORGANISM: Artificial Sequence
```

```
-continued

<220> FEATURE:
<223> OTHER INFORMATION: primer MDB356

<400> SEQUENCE: 13
aatcctgttg ccggtcttgc g                                              21

<210> SEQ ID NO 14
<211> LENGTH: 22
<212> TYPE: DNA
<213> ORGANISM: Artificial Sequence
<220> FEATURE:
<223> OTHER INFORMATION: primer DPA017

<400> SEQUENCE: 14
gattagagtc ccgcaattat ac                                             22

<210> SEQ ID NO 15
<211> LENGTH: 20
<212> TYPE: DNA
<213> ORGANISM: Artificial Sequence
<220> FEATURE:
<223> OTHER INFORMATION: primer MLD019

<400> SEQUENCE: 15
caagatgcga gcaactatgt                                                20

<210> SEQ ID NO 16
<211> LENGTH: 200
<212> TYPE: DNA
<213> ORGANISM: Artificial Sequence
<220> FEATURE:
<223> OTHER INFORMATION: sequence comprising target site deletion

<400> SEQUENCE: 16
tcttggacca caattttgag cttttcattt tctattttga ggataatagt ttattccctc    60
aaggaactat tcaactgagc ttaatatctc aattttttt aacatatgac tataagtatc   120
ctccaaatat ttaaaagaa tatcaccatt atccgaatct tctttaaaat ctgttagaac   180
acggtttgga atagtggtag                                              200

<210> SEQ ID NO 17
<211> LENGTH: 21
<212> TYPE: DNA
<213> ORGANISM: Artificial Sequence
<220> FEATURE:
<223> OTHER INFORMATION: primer GHI01

<400> SEQUENCE: 17
aacctaggct gctgaaggag c                                              21

<210> SEQ ID NO 18
<211> LENGTH: 21
<212> TYPE: DNA
<213> ORGANISM: Artificial Sequence
<220> FEATURE:
<223> OTHER INFORMATION: primer GHI02

<400> SEQUENCE: 18
caactcctcc agtcatctcc g                                              21
```